(12) United States Patent
Yoneda et al.

(10) Patent No.: US 6,945,674 B2
(45) Date of Patent: Sep. 20, 2005

(54) LIGHT IRRADIATING UNIT

(75) Inventors: Kenji Yoneda, Kyoto (JP); Takashi Sugita, Kyoto (JP); Kenji Miura, Kyoto (JP); Shigeki Masumura, Kyoto (JP)

(73) Assignee: CCS, Inc., Kyoto (JP)

( * ) Notice: Subject to any disclaimer, the term of this patent is extended or adjusted under 35 U.S.C. 154(b) by 66 days.

(21) Appl. No.: 10/618,551

(22) Filed: Jul. 11, 2003

(65) Prior Publication Data

US 2004/0012965 A1 Jan. 22, 2004

(30) Foreign Application Priority Data

Jul. 16, 2002 (JP) ...................................... P2002-207401

(51) Int. Cl.[7] ............................ F21V 29/00; G02B 6/00
(52) U.S. Cl. ...................... 362/294; 362/555; 362/558; 362/580
(58) Field of Search .............................. 362/294, 373, 362/551, 555, 556, 547, 580, 581, 572, 575; 385/39, 74; 257/706, 712; 174/16.1, 16.3, 252; 165/104.334

(56) References Cited

U.S. PATENT DOCUMENTS 4,431,267 A 2/1984 Finck et al.

6,070,997 A 6/2000 Duke et al.
6,595,674 B1 7/2003 Yoneda

FOREIGN PATENT DOCUMENTS

| JP | 62-036749 | 2/1987 |
|----|-----------|--------|
| JP | 01-72339 | 3/1989 |
| JP | 06-259798 | 9/1994 |
| JP | 08-186322 | 7/1996 |
| JP | 11-53096 | 2/1999 |
| JP | 11-202161 | 7/1999 |
| JP | 2000-269581 | 9/2000 |

*Primary Examiner*—Sandra O'Shea
*Assistant Examiner*—Guiyoung Lee (57) ABSTRACT

A light irradiating unit comprises an LED 5 and a housing 2 into which the LED 5 is incorporated and that has a heat dissipating portion wherein the housing 2 has a first housing element 21 and a second housing element 22 each of which is joined serially along a predetermined axial line, and further comprises a pressing arrangement 3 that fixes the LED 5 with pressure between a first pressing face 3b arranged at the first housing element 21 side and a second pressing face 3a arranged at the second housing element 22 side accompanied by joining the first and the second housing elements 21, 22 and a positioning arrangement 4 that positions the LED 5 so as to align an optical axis of the LED 5 with the predetermined axial line accompanied by joining the first and the second housing elements 21, 22.

32 Claims, 7 Drawing Sheets

Temperature/Illumination Intensity Change of Light Irradiating Unit

| | conventional arrangement (with heat dissipating sheet) | this invention no heat dissipating sheet (loosely joined) | this invention no heat dissipating sheet (tightly joined) |
|---|---|---|---|
| initial temperature of soldered face (°C) | 24.2 | 25.5 | 27.2 |
| soldered face temperature 60 min later | 55.7 | 57.1 | 49.3 |
| temperature rise (°C) | 31.5 | 31.6 | 22.1 |
| initial temperature of housing (°C) | 24.3 | 25.4 | 26.8 |
| housing temperature 60 min later (°C) | 47 | 54.1 | 44.6 |
| temperature rise (°C) | 22.7 | 28.7 | 17.8 |
| initial illumination intensity (lx) | 134200 | 138000 | 138200 |
| illumination intensity 60 min later (lx) | 79200 | 97600 | 112000 |
| deterioration rate | 59% | 71% | 81% |

Temperature/Illumination Intesity Change of Light Irradiatin Unit

| | conventional arrangement (red) | this invention (red) (tihgtly joined) |
|---|---|---|
| initial temperature of soldered face (°C) | 25 | 27 |
| soldered face temperature 60 min later | 44 | 41 |
| temperature rise (°C) | 19 | 14 |
| initial temperature of housing (°C) | 25 | 27 |
| housing temperature 60 min later (°C) | 40 | 39 |
| temperature rise (°C) | 15 | 12 |
| initial illumination intensity (lx) | 155400 | 186900 |
| illumination intensity 60 min later (lx) | 129100 | 170300 |
| deterioration rate | 83% | 91% |

Fig.6

Temperature Change of Light Irradiating Unit

| | this invention (blue) (loosely joined) | this invention (blue) (tightly joined) |
|---|---|---|
| initial temperature of soldered face (°C) | 23 | 20.9 |
| soldered face temperature | 46 | 41.4 |
| temperature rise (°C) | 23 | 20.5 |
| initial temperature of housing (°C) | 23 | 20.9 |
| housing temperature 60 min later (°C) | 40 | 36.6 |
| temperature rise (°C) | 17 | 15.7 |

Fig. 7

LIGHT IRRADIATING UNIT

BACKGROUND OF THE INVENTION AND RELATED ART STATEMENT

The present claimed invention relates to a light irradiating unit, more specifically to a light irradiating unit that is preferably used to inspect an appearance or a flaw of a product by irradiating light in a factory or the like.

Conventionally, a halogen lamp is used as a light source for this kind of a light irradiating unit. Considering an efficiency or an accuracy in product inspection, however, the halogen lamp as a light source is not suitable to get enough stability in luminous intensity, life duration and a quick responsive characteristics. A plurality of LEDs are used as a new light source to solve this problem. More specifically, generally known is like a light irradiating unit that the present claimed inventor has invented and shown in Japan Patent Laid Open No. 2000-21206 in which a plurality of LEDs are arranged on a print substrate and light is introduced by the plurality of LEDs through a bunch of optical fibers or a plurality of LEDs are arranged on a concave face of a cone shape and light irradiated from the LEDs is directly focused. The reason why a plurality of LEDs are used is based on a fact that it is difficult for an LED in an elementary substance to obtain enough light volume.

Recently a light emitting element referred to as a power LED that can produce big light volume in an elementary substance has been developed. This power LED can flow electric current of several hundred mA and can produce light volume corresponding to the electric current unlike a conventional LED that can flow electric current of several dozen mA at most.

The above-mentioned power LED makes it possible to downsize a light source, thereby to provide a new usage and a new possibility.

With the power LED, however, heat dissipation is indispensable because of a heat problem due to a huge electric current. LEDs generally have low light volume and short life duration at a high temperature. Conventionally in a case wherein a plurality of LEDs are used, each LEDs is mounted on a substrate, which is also to simplify a process of fixing the LEDs, and big electric current does not flow each LEDs in an elementary substance and each LED is arranged separately. Then the heat problem can be solved by mounting the substrate on a housing having heat dissipating fins. The power LED has dissipated heat through a substrate made of aluminum, however, there is a limit to dissipate heat generated from a bare chip of the power LED because the aluminum substrate dissipates heat through a glass epoxy layer (heat conductivity 0.3~0.4 W/mk) that is arranged for insulation. As a result, just adopting the power LED will increase the heat dissipating portion in size, which fails to downsize the light source.

Further, since there is also a limit to position the power LED accurately in mounting the power LED on the substrate with soldering, a positioning relationship of the substrate and the power LED is not uniform even though the substrate is mounted on the housing with positioning accurately. As a result, for example, it might fail to introduce light from the power LED into a light introducing end portion of an optical fiber accurately, thereby to generate a loss in light volume at the light introducing end portion and to loose benefit of the above-mentioned big light volume. In order to prevent this with a simple arrangement, time and a cost to assemble the light source might increase.

In order to solve all of the above problems, the present claimed invention mainly intends to provide a light irradiating unit wherein a power LED is used as a light source so as to contribute to a characteristics of heat dissipation, downsizing, simplifying an assembling process and an accuracy of illuminating light.

SUMMARY OF THE INVENTION

The light irradiating unit in accordance with the present claimed invention comprises an LED and a housing into which the LED is incorporated and which has a heat dissipating portion wherein the housing has a first housing element and a second housing element each of which is joined serially along a predetermined axial line, and is characterized by further comprising a pressing arrangement that fixes the LED with pressure between a first pressing face arranged at the first housing element side and a second pressing face arranged at the second housing element side accompanied by joining the first and the second housing elements and a positioning arrangement that positions the LED so as to align an optical axis of the LED with the predetermined axial line accompanied by joining the first and the second housing elements.

In accordance with the arrangement, a process of fixing the LED with pressure by the pressing arrangement and a process of positioning the LED by the positioning arrangement are conducted at once when the first housing element is joined to the second housing element. As a result, it is possible to simplify an assembling of the light irradiating unit and to set the light irradiated from the LED with accuracy. In addition, since the LED makes a tight contact with the housing having the heat dissipating portion directly or indirectly through some sort of an intervening member, it is possible to dissipate heat extremely effectively without making a size of the housing unnecessarily bulky. For example, silicone grease may be applied as the intervening member that is a thermal conduction member that improves adhesiveness and heat conductivity by absorbing roughness of the faces between each pressing faces and the LED.

As a concrete shape wherein an effect of the present claimed invention is especially outstanding represented is the LED in an elementary substance that can flow an electrical current not lower than 200 mA through 300 mA in a stationary state.

In order to keep a pressed state in a good condition it is preferable that an elastic member is arranged between at least one of the first and the second pressing faces and the LED.

As a concrete shape of the second pressing face represented is that the second housing element comprises a wall and a projecting body projecting from the wall and the second pressing face is set at a surface that faces to the first housing element on the projecting body. In this case, the projecting body may not be integrated into the wall. For some LED insulation is required to provide between the LED and a wall of a housing, in which case the projecting body alone may be of material having an insulating characteristics.

In case it is preferable to mount a substrate on an LED in association with wiring or a resistance to be loaded, a substrate may be an annular and the projecting body may be tightly attached to a bottom face of the LED with penetrating a center hole of the substrate.

As a concrete shape of the positioning arrangement represented is that the positioning arrangement makes use of a ring portion mounted on the housing and positions the LED by inserting a center through hole of the ring portion over a periphery of the LED without a slack accompanied by joining the first housing element to the second housing element.

In this case if an inner face of the ring portion is a mirror finished conic concave face and the ring portion has a function to guide light forward, the positioning arrangement serves also as a function of light reflecting function, thereby to reduce a number of components and to simplify an arrangement.

In addition, if the light irradiating unit further comprises a lens mechanism that is incorporated into the housing and is so arranged that the light irradiated from the LED is focused on a light focusing portion arranged at a predetermined portion in a size of a predetermined radius through the lens mechanism, a light introducing end portion of a light guiding member such as optical fibers (a bunch) or a glass rod can be arranged at the light focusing portion and light can be effectively irradiated from a light irradiating end of the light guiding member.

For a light irradiating unit that further comprises a lens mechanism incorporated into the housing, in order to form the positioning arrangement by making use of the lens mechanism and to reduce a number of components without difficulty so as to simplify an arrangement, it is preferable that the positioning arrangement is so arranged to position the LED by inserting the LED without a slack into a concave portion arranged on a lens constituting the lens mechanism.

As a preferable shape of the lens mechanism to focus light represented is that the lens mechanism comprises a first lens that makes the light irradiated from the LED generally parallel and a second lens that focuses the light from the first lens into the light focusing portion.

As a preferable shape of the heat dissipating portion represented is that the heat dissipating portion is in a shape of a fin arranged on a periphery portion of the housing.

DETAILED DESCRIPTION OF THE PREFERRED EMBODIMENTS

A first embodiment of the present claimed invention will be described with reference to the drawings.

Figure 1:
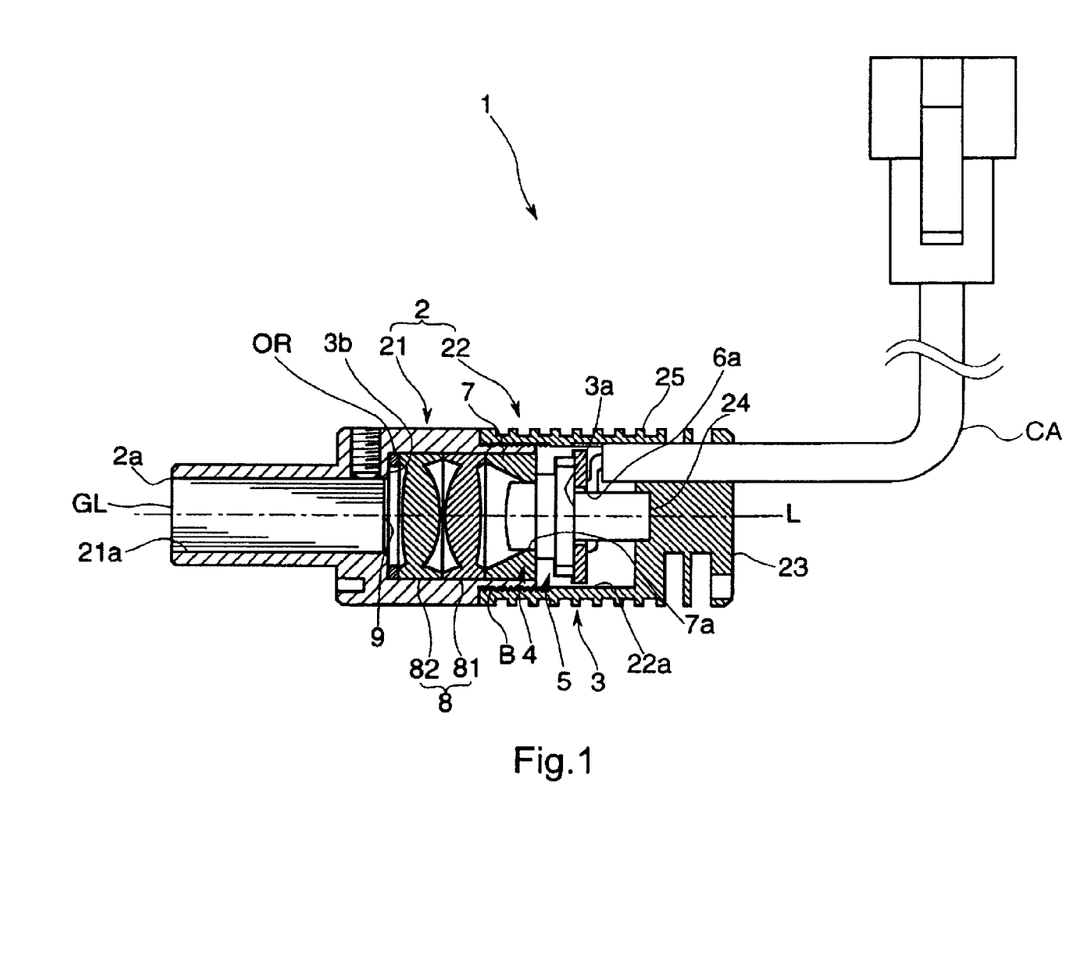
FIG. 1 is a longitudinal cross-sectional view showing an internal arrangement of a light irradiating unit in accordance with a first embodiment of the present claimed invention.

A light irradiating unit 1 in accordance with the embodiment comprises, as shown in FIG. 1, an LED 5 in an elementary substance and a housing 2 into which the LED 5 is incorporated and that has a heat dissipating fin 25 as a heat dissipating portion. The light irradiating unit 1 irradiates light irradiated from the LED 5 through a light irradiating exit 2a arranged on an end face of the housing 2.

Figure 2:
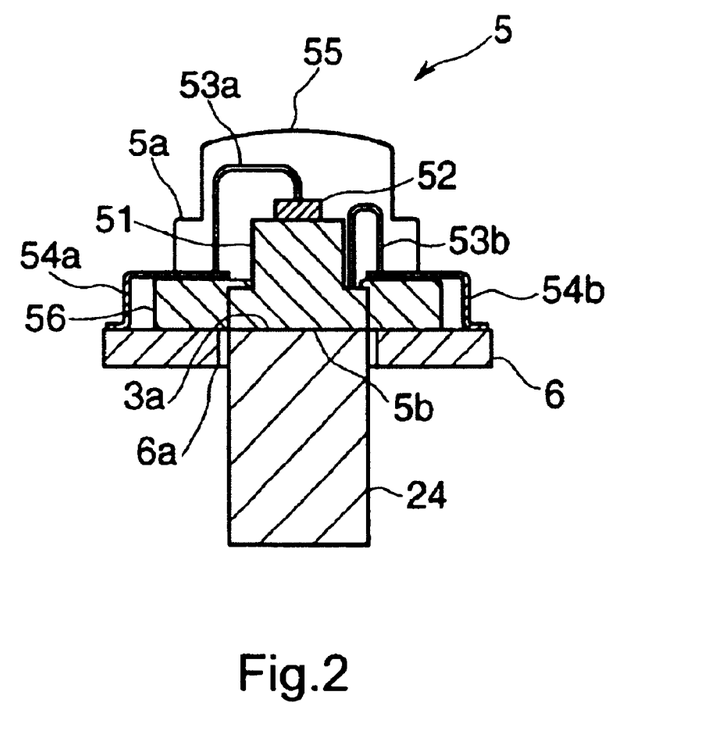
FIG. 2 is a longitudinal cross-sectional view showing an LED and a substrate in accordance with the embodiment.

The LED 5 comprises, as shown in FIG. 2, an electric conductor 51 that also serves as a heat conductor made of metal (for example, copper), a single LED chip 52 that is fixed to the electric conductor 51 with a die bonding or the like, a resin frame 56 that supports the electric conductor 51 by inserting over the electric conductor 51, two pieces of lead wires 53a, 53b (also called as bonding wires) each of whose one end is connected to an electrode of a cathode side (not shown in drawings) or an electrode of an anode side (not shown in drawings) of the LED chip 52 directly or indirectly through the electric conductor 51, a pair of electrodes 54a, 54b to which the other end of each lead wires 53a, 53b is connected and a resin mold portion 55 made of material having transparency (plastic such as epoxy or silicone, elastomer or glass) to tightly seal and protect a part of the LED chip 52, the lead wires 53a, 53b and the electrodes 54a, 54b, wherein all of the above are united so as to be a product so called "a power LED 5". The LED 5 can flow an electric current of not less than 300 mA continuously for a predetermined period and emits quite a big amount of light by itself compared with a conventional LED. In this embodiment, a glass epoxy substrate 6 having a toric shape is mounted on a bottom face of the resin frame 56 and the electrodes 54a, 54b are connected with a power cable CA through the glass epoxy substrate 6.

The housing 2 is, as shown in FIG. 1, in a hollow shape having a first housing element 21 and a second housing element 22 each of which is joined serially along a center axial line L as a predetermined axial line with a screw portion B formed at a bonded portion of the first and the second housing elements 21 and 22.

The first housing element 21 is in a cylinder shape having a through hole 21a that penetrates along the axial line L and one end of the opening of the through hole 21a is the light irradiating exit 2a. The through hole 21a comprises a small diameter portion formed in the light irradiating exit 2a side and a big diameter portion formed in the other side. In this embodiment a glass rod GL as a light guiding member is fittingly inserted into the small diameter portion. An O ring OR as an elastic member, a lens mechanism 8 and a ring portion 7 are fittingly inserted in sequence from a back with centering on the axial line L without a slack along a radial direction. The lens mechanism 8 comprises a first lens 81 and a second lens 82, each of which is arranged serially along the axial line L. The first lens 81 makes light irradiated from the LED 5 generally parallel and the second lens 82 focuses light from the first lens 81 on a light focusing portion 9 arranged at a portion where a proximal end face of the glass rod GL locates so as to make the focused light in a size generally the same radius as an effective radius of the glass rod GL. The ring portion 7 is made of metal or resin in a shape wherein an inner face of the ring portion 7 diverges outward toward a traveling direction of the light and the inner face is mirror finished.

The second housing element 22 is a circular shape in a cross sectional view having a hole with a bottom 22a opening at an end face locating in the first housing element 21 side and comprises a wall 23 having a side wall and a bottom wall and a cylindrical projecting body 24 extending from a center of the bottom wall along the axial line L toward the first housing element 21 side. A plurality of grooves having a bottom are arranged to form a heat dissipating fin 25 on a periphery of the second housing element 22. It is a matter of course that the heat dissipating fin 25 may be arranged on the first housing element 21.

In this embodiment further provided are a pressing arrangement 3 that fixes the LED 5 with pressure between a first pressing face 3b arranged at the first housing element 21 side and a second pressing face 3a arranged at the second housing element 22 side accompanied by joining the first housing element 21 to the second housing element 22 and a positioning arrangement 4 that positions the LED 5 so as to align an optical axis of the LED 5 with the axial line L accompanied by joining the first housing element 21 to the second housing element 22.

The first pressing face 3b of the pressing arrangement 3 is set at a part of a surface of a stepped portion that locates at a boundary between the small diameter portion and the big diameter portion of the first housing element 21 and that faces to the second housing element 22. The first pressing face 3b is so arranged to press a stepped portion 5a (shown in FIG. 2) arranged on a resin mold portion of the LED 5 through the O ring OR, the lens mechanism 8 and the ring portion 7. The second pressing face 3a is set at a distal end face of the projecting body 24 of the second housing element 22 and so arranged to press a bottom face 5b of the electric conductor 51 of the LED 5. The lens mechanism 8 is given a pressing force by the first pressing face 3b, however, the O ring OR stands between the first pressing face 3b and the lens mechanism 8 and acts as an elastic member, which prevents the lens 81, 82 from being broken when joining the first and the second housing elements 21, 22 and which also prevents fluctuation of the pressing force by creating a constant pressure, thereby to keep a pressing condition stable.

The positioning arrangement 4 is so arranged that a center through hole 7a of the ring portion 7 fits over the peripheral of the LED 5 generally without a gap accompanied by joining the first housing element 21 to the second housing element 22 so as to align an optical axis of the light irradiated from the LED 5 with the axial line L. More concretely, an opening portion of the bottom face of the ring portion 7 fits over a peripheral face of the resin mold portion 55 of the LED 5 without a slack so as to make positioning of the ring portion 7.

A method for assembling the light irradiating unit 1 having the above arrangement will be briefly explained.

First, the glass rod GL, the O ring OR, the lens mechanism 8 and the ring portion 7 are incorporated into the first housing element 21. Meanwhile, the LED 5 loaded with the substrate 6 and the power cable CA is placed on the second housing element 22 with the bottom face of the LED 5 tightly attached to the distal end face 3a of the projecting body 24.

Next, the first housing element 21 is joined to the second housing element 22. With this process, the first housing element 21 approaches to the second housing element 22, followed by positioning the opening portion of the bottom face of the ring portion 7 along a radial direction to the axial line L by fittingly inserting the opening portion over the distal end portion of the LED 5. As a further process of joining the first housing element 21 to the second housing element 22, each of the pressing faces 3a, 3b presses the LED 5 along the axial line L from a direction facing each other and fixes the LED 5 with pressure. The substrate 6 has a center hole 6a whose diameter is larger than that of the projecting body 24 and an external diameter of the substrate 6 is smaller than an internal diameter of the second housing element 22 so that the LED 5 is positioned along the radial direction by the positioning arrangement 4 alone and other arrangement does not interfere positioning of the LED 5.

More specifically, in accordance with the embodiment, the LED 5 can automatically and simultaneously be both fixed and positioned accurately due to an action of the pressing arrangement 3 and the positioning arrangement 4 arranged inside the first and the second housing elements 21, 22 just by joining the first housing element 21 to the second housing element 22. As a result of this, since assembling is extremely simplified and the LED 5 directly contacts the housing 2 having the heat dissipating portion, a speed of dissipating heat is festinated and heat is dissipated quickly. Then luminance can be prevented from deterioration because of an effect of lowering junction temperature of the LED 5 and the LED 5 can have a long life. In addition, since the LED 5 can be positioned accurately and the light can be irradiated on the light focusing portion 9 without fail, transmission loss in the glass rod GL as the light guiding member can be reduced as much as possible.

Figure 3:
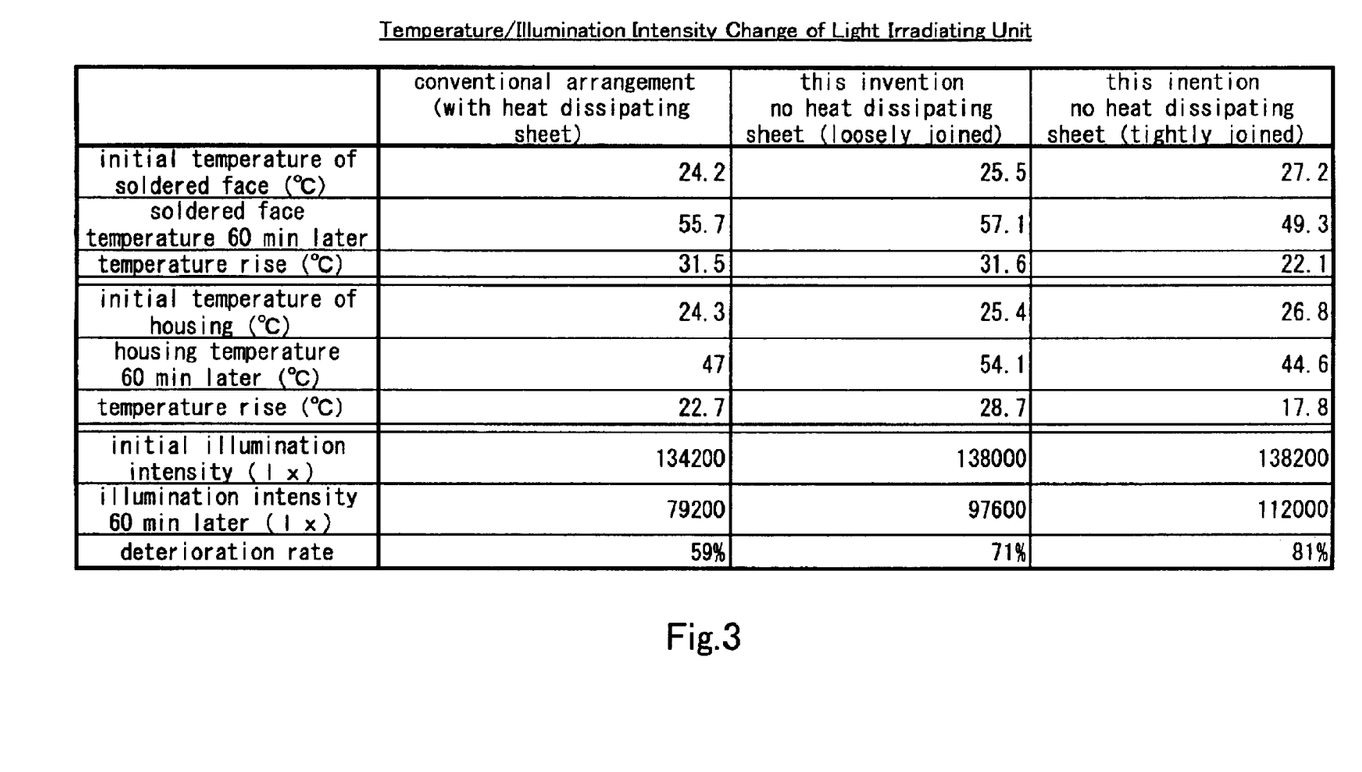
FIG. 3 is an explanatory table showing effects of the light irradiating unit in accordance with the embodiment.

An effect of dissipating heat by the pressing arrangement 3 is, as shown in FIG. 3, very conspicuous from an experimental result. More specifically, when we compare a deterioration of an illumination intensity, for example, from an initial state to 60 minutes later between a state (B) in which the pressing faces 3a, 3b are just brought into contact with the LED 5 and a state (C) in which the LED 5 is fixed with pressure by the pressing faces 3a, 3b, the state (C) demonstrates less deterioration of the illumination intensity than the state (B) and the state (C) produces an effect. In order to improve adhesiveness and heat conductivity by absorbing roughness of the faces between each pressing faces 3a, 3b and the LED 5, silicone grease is applied to the pressing faces 3a, 3b and the LED 5. However, the pressing faces 3a, 3b are attached to the LED 5 generally directly. In this case, when we compare deterioration of the illumination intensity between the states (B), (C) and a state (A) wherein a heat dissipating sheet is arranged between the pressing faces 3a, 3b and the LED, the states (B) and (C) demonstrate less deterioration of illumination intensity than the state (A).

Further, in this embodiment, since the electric conductor 51 of the LED 5 is exposed to outside from the bottom face of the LED 5, insulation has to be provided between the LED 5 and the wall 23 of the housing 2 in order to dissipate heat by contacting the bottom face of the LED 5 with the housing 2. However, since the projecting body 24 is arranged between the LED 5 and the wall 23, insulation can be provided by processing the projecting body 24 alone or by selecting a material of the projecting body 24. More specifically, there is no need of providing a process of insulation for whole of the second housing element 22, and it is also possible to reduce a necessary amount of material such as aluminum nitride that is expensive and high in thermal conductivity and insulation properties.

In addition, the ring portion 7 also serves as a function of a reflecting member of the light irradiated from the LED 5, a function of the positioning arrangement 4 and a function of the pressing arrangement 3, which makes it possible to reduce a number of components and to contribute to simplification of the arrangement.

A second embodiment of the present claimed invention will be explained with reference to FIG. 4 and FIG. 5.

Figure 4:
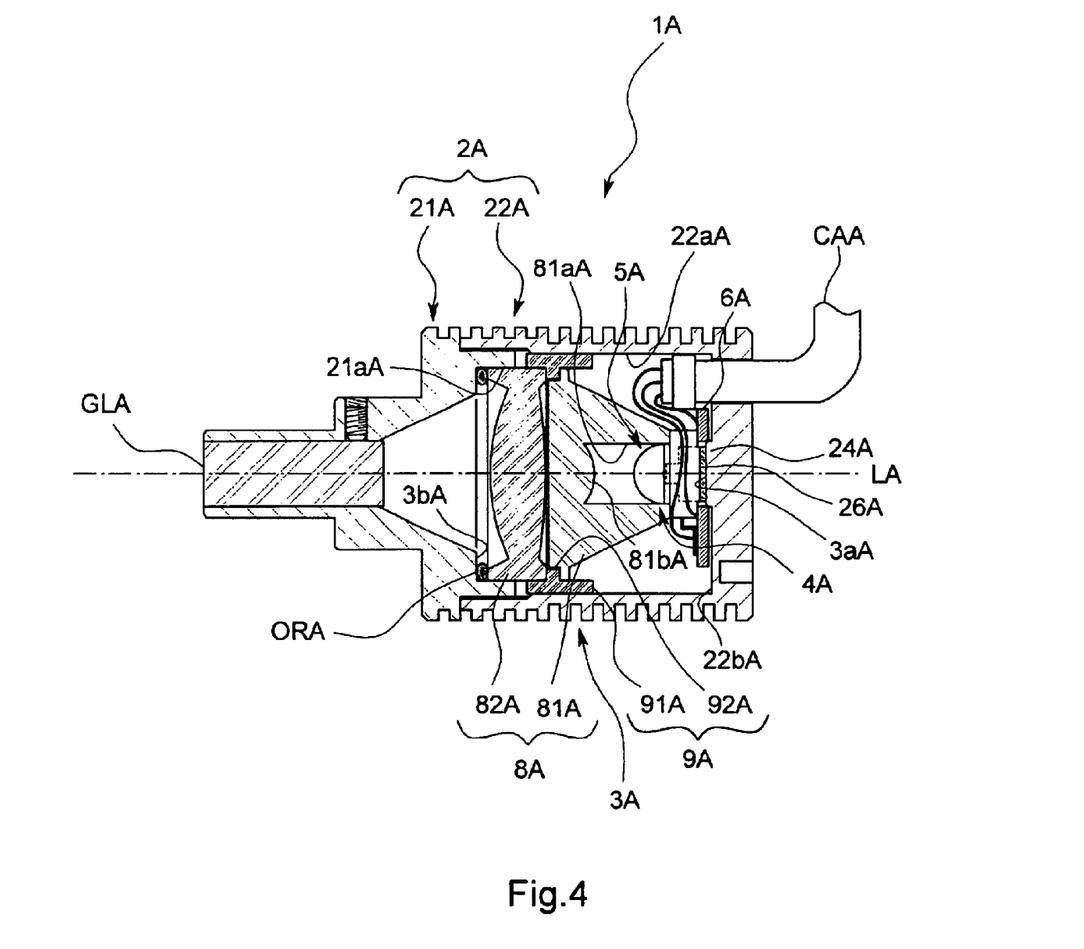
FIG. 4 is a longitudinal cross-sectional view showing an internal arrangement of a light irradiating unit in accordance with a second embodiment of the present claimed invention.
Figure 5:
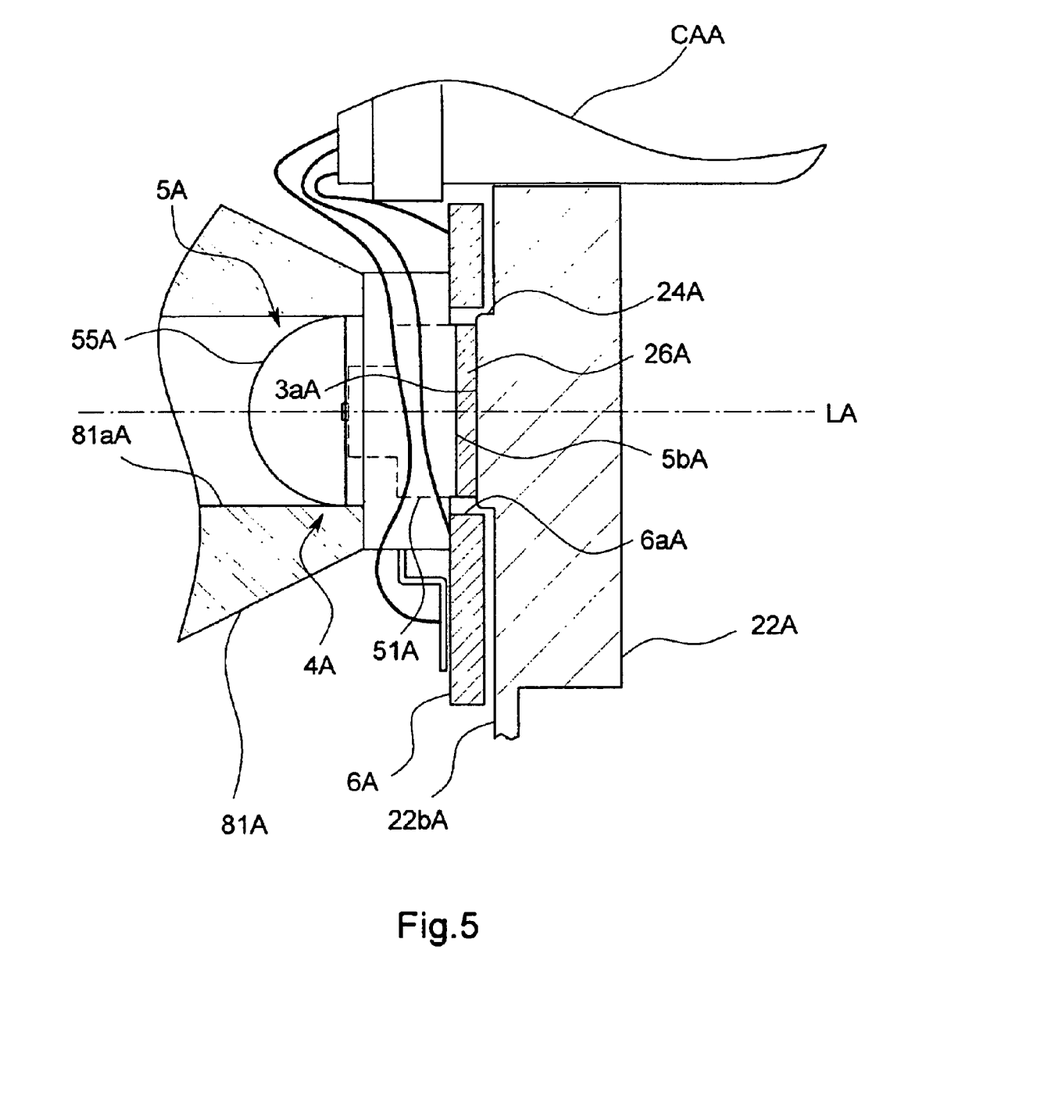
FIG. 5 is a longitudinal cross-sectional view showing an LED and a substrate in accordance with the embodiment.

A light irradiating unit 1A in accordance with the second embodiment is, as shown in FIG. 4, so arranged that an LED 5A is incorporated into a housing 2A and like the above mentioned first embodiment comprises a pressing mechanism 3A that fixes the LED 5A with pressure between a first pressing face 3bA arranged at the first housing element 21A side and the second pressing face 3aA arranged at the second housing element 22A side accompanied by joining the first housing element 21A to the second housing element 22A and a positioning arrangement 4A that positions the LED 5A so as to align an optical axis of light irradiated from the LED 5A with a center axial line AL as a predetermined axial line accompanied by joining the first and the second housing element 21A, 22A.

Each components will be explained with clarifying differences between the light irradiating unit 1 of the first embodiment and that of this embodiment.

The housing 2A is, as described above, in a hollow cylinder shape having the first housing element 21A and the second housing element 22A and inside of which the LED 5A and a lens mechanism 8A are accommodated.

Since the first housing element 21A has generally the same arrangement as that of the first embodiment, an explanation is omitted. The second housing element 22A has the same arrangement as that of the above first embodiment comprising a side wall 22aA, a bottom wall 22bA and a cylindrical projecting body 24A apart from the projecting body 24A integrally formed with the bottom wall 22bA.

The LED 5A is different slightly from the first embodiment in an outer shape such as a resin mold 55A to protect LED chips is hemisphere. The code 5bA in FIG. 5 is a bottom face of the electric conductor exposed to outside from a center of the bottom face of the resin mold 55A like the LED 5 in the first embodiment, and an annular substrate 6A is arranged to surround the bottom face 5bA of the resin mold 55A.

The lens mechanism 8A comprises a first lens 81A, a second lens 82A and a spacer 9A arranged between the first lens 81A and the second lens 82A.

The first lens 81A is a transparent body, for example, made of resin, generally in a shape of a cone frustum and arranged to fittingly insert a peripheral face of the first lens 81A into an inner face of the second housing element 22A through the spacer 9A without a slack along a radial direction with aligning its center axis with an axial line LA of the second housing element 22A.

The second lens 82A is the same as that of the first embodiment and so arranged that a half of the second lens 82A is inserted into a big diameter portion 21aA of the first housing element 21A without a slack along a radial direction and other half thereof is fittingly inserted into an inner face of the second housing element 22A through the spacer 9A so as to align its center axis with the axial line LA and to align the first housing element 21A with the second housing element 22A as well. An O ring ORA is arranged between a bottom face of the big diameter portion 21aA and the second lens 82A.

The spacer 9A comprises a cylindrical spacer body 91A and an annular projecting portion 92A integrally projecting inward from a general center of the inner face of the spacer body 91A. The spacer 9A is so arranged that surfaces facing each other back to back of the projecting portion 92A make a contact with an edge face of a peripheral portion of the first and the second lens 81A, 82A to give distance between the first lens 81A and the second lens 82A and to reduce friction between the first lens 81A and the second lens 82A so as to prevent a running torque from transmitting to the LED 5A through the first lens 81A when each of the housing elements 21A, 22A is joined. A material of the spacer 9A is metal or resin and preferably small in frictional properties.

The first pressing face 3bA of the pressing arrangement 3A is, like the above first embodiment, set at a surface of a stepped portion that is arranged on an inner face of the big diameter portion 21aA of the first housing element 21A and that faces to the second housing element 22A, more specifically, set at a face where the first housing element 21A makes a contact with the O ring ORA. The second pressing face 3aA is, like the above first embodiment, set at a surface of the projecting body 24A of the second housing element 22A that faces to the first housing element 21A, more specifically, set at a distal end face of the projecting body 24A.

The first pressing face 3bA and the second pressing face 3aA approach each other along the center axial line LA accompanied by joining the first housing element 21A to the second housing element 22A so as to press the LED 5A with the first pressing face 3bA through the O ring ORA and the lens mechanism 8A and with the second pressing face 3aA through a heat conductor 26A. The heat conductor 26A is arranged between the bottom face 5bA of the LED 5A and the second pressing face 3aA of the second housing element 22A and preferably made of a material that is high in thermal conductivity and electrically insulated such as aluminum nitride, heat dissipating molten resin and liquid ceramics.

The positioning arrangement 4A in accordance with this embodiment comprises a concave portion 81aA whose cross sectional view is a circular form opening toward an end face of a small diameter portion of the first lens 81A and a resin mold 55A of the LED 5A that is inserted into the concave portion 81aA. The LED 5A is positioned along a radial direction with aligning the optical axis of the LED 5A with the axial line LA by fittingly inserting the resin mold 55A into the concave portion 81aA accompanied by joining the first housing element 21A to the second housing element 22A.

The concave portion 81aA is so arranged that its bottom face is formed to be an evaginated curved face to be an inflective portion 81bA. Light within a predetermined angle from the optical axis of the light irradiated from the LED 5A is inflected to be parallel by the inflective portion 81bA while other light diverging out of the predetermined angle is reflected against a boundary face of a periphery of the first lens 81A. As a result, most light irradiated from the LED 5A is effectively paralleled to travel toward a direction of the optical axis.

A method for assembling the light irradiating unit 1A having the above arrangement will be briefly explained by citing an example.

First, the glass rod GLA, the O ring ORA, the second lens 82A and the spacer 9A are incorporated into the first housing element 21A. In the meantime, the first lens 81A is mounted on the LED 5A loaded with the substrate 6A and a power cable CAA and then the LED 5A is placed on the second housing element 22A so that the bottom face 5bA of the LED 5A tightly attaches to the second housing element 22A through the thermal conductor 26A when the first and the second housing elements 21A and 22A are joined.

Next, the first housing element 21A is joined to the second housing element 22A. With this process, the first pressing face 3bA approaches to the second pressing face 3aA, followed by fixing each components, namely the O ring ORA, the lens mechanism 8A, LED 5A and the thermal conductor 26A, inside the housing 2A with pressure.

The LED 5A is positioned to align its optical axis with the axial line LA along a radial direction by fittingly inserting the resin mold 55A of the LED 5A into the concave portion 8aA without a slack accompanied by joining the first and the second housing elements 21A, 22A. In this case, since a small gap is formed between a center hole 6aA of the substrate 6A and the projecting body 24A, the substrate 6A and the projecting body 24A do not block positioning of the LED 5A by the positioning arrangement 4A.

In accordance with the embodiment, the same effect as that of the first embodiment can be produced and especially in this embodiment since the LED 5A is positioned by making use of the concave portion 81aA arranged on the first lens 81A, a number of components can be reduced with ease, thereby to simplify the arrangement.

Figure 6:
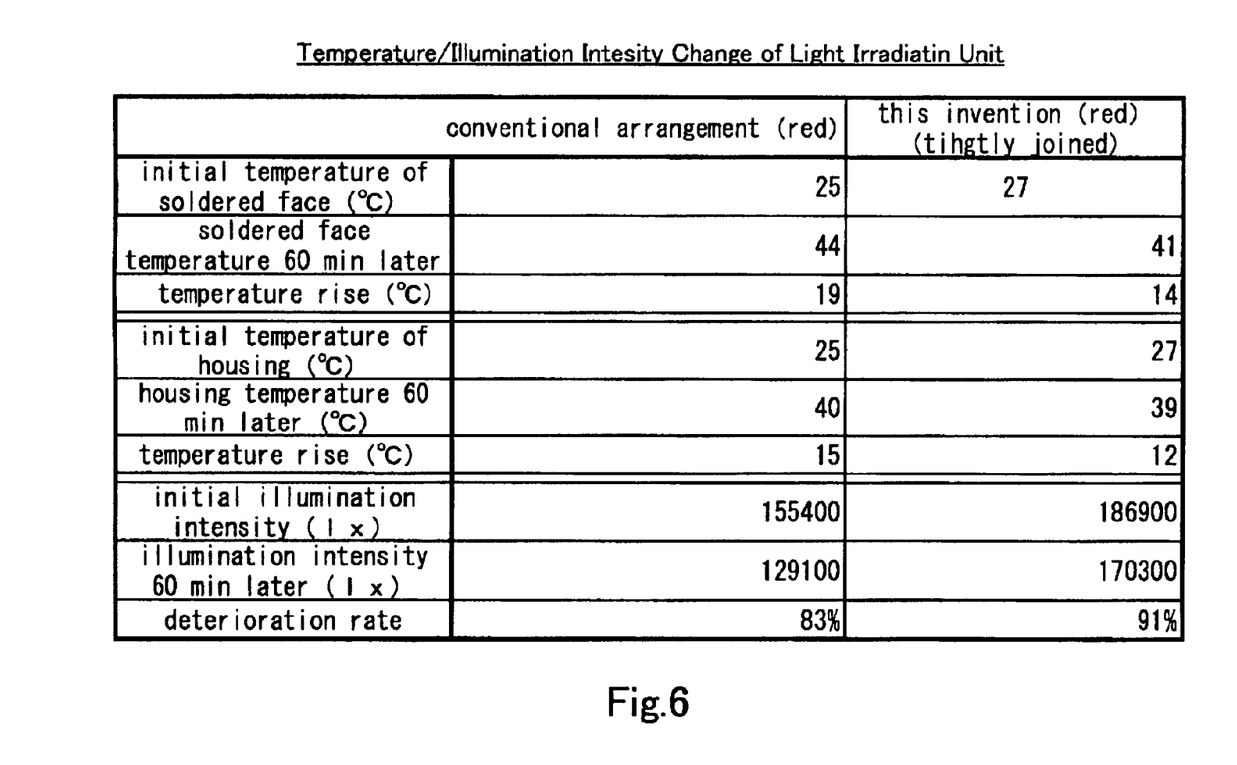
FIG. 6 is an explanatory table showing effects of the light irradiating unit in accordance with the embodiment.
Figure 7:
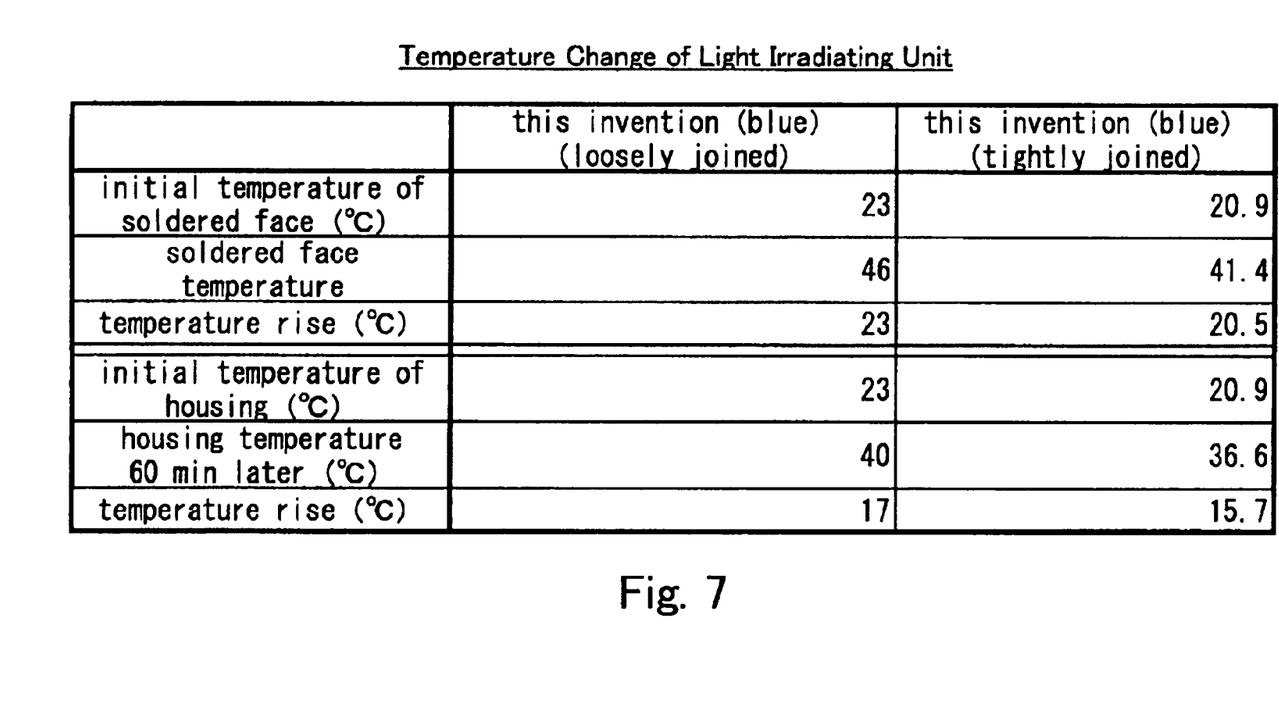
FIG. 7 is an explanatory table showing effects of the light irradiating unit in accordance with the embodiment.

Numerical data of concrete effects on heat dissipation will be given. FIG. 6 and FIG. 7 show result on a red LED and a blue LED cases respectively. In case of the red LED comparison is conducted between an arrangement wherein heat is dissipated through an aluminium substrate having a glass epoxy layer on its surface (conventional arrangement) and an arrangement wherein the red LED is joined with enough pressure (the tightly joined red LED in accordance with the present claimed invention). The arrangement in accordance with the invention clearly demonstrates a small rise in temperature of both a soldered face and the housing and a small deterioration in illumination intensity. In case of the blue LED comparison is conducted between an arrangement wherein the blue LED is joined with big pressure (the tightly joined blue LED in accordance with the present claimed invention) and an arrangement wherein the blue LED is joined with small pressure (the loosely joined blue LED in accordance with the present claimed invention). The blue LED joined with big pressure demonstrates a small rise in temperature.

The present claimed invention is not limited to the above embodiments and may be variously varied.

For example, it is a matter of course that the pressing arrangement can be varied in accordance with a shape of the LED or a shape of the housing.

The substrate 6 may be omitted in some case. The LED in an elementary substance may have a plurality of LED chips. The glass rod is used as a light guiding member, however, a bundle of optic fibers may be used instead of the glass rod, and the glass rod may be omitted.

Further, for example, a flexible gap filler that produces high thermal conductivity and that is electrically insulated may be arranged between the housing and the LED not to make the housing contact with the LED directly. It is a matter of course that the light irradiating unit may be used as a lighting but may be used for another usage such as to promote chemical reaction.

As mentioned above, a process of fixing the LED with pressure by the pressing arrangement and a process of positioning the LED by the positioning arrangement can be conducted at once when the first housing element is joined to the second housing element. As a result of this, it is possible to simplify an assembling the light irradiating unit, to set the light irradiated from the LED with accuracy, to prevent deterioration of the luminance due to an effect of lowering a junction temperature because the housing having the heat dissipating portion directly contacts the LED and to elongate life duration.

What is claimed is:

1. A light irradiating unit comprising an LED and a housing into which the LED is incorporated and which has a heat dissipating portion wherein the housing has a first housing element and a second housing element each of which is joined serially along a predetermined axial line,
   and further comprising a pressing arrangement that fixes the LED with pressure between a first pressing face arranged at the first housing element side and a second pressing face arranged at the second housing element side accompanied by joining the first and the second housing elements and a positioning arrangement that positions the LED so as to align an optical axis of the LED with the predetermined axial line accompanied by joining the first and the second housing elements, wherein the LED in an elementary substance can flow electrical current not lower than 200 mA through 300 mA in a stationary state.

2. The light irradiating unit according to claim 1, wherein the light irradiating unit further comprises a lens mechanism that is incorporated into the housing and is so arranged that the light irradiated from the LED is focused on a light focusing portion arranged at a predetermined portion in a size of a predetermined radius through the lens mechanism.

3. The light irradiating unit according to claim 2, wherein the lens mechanism comprises a first lens that makes the light irradiated from the LED generally parallel and a second lens that focuses the light from the first lens into the light focusing portion.

4. The light irradiating unit according to claim 1, wherein the heat dissipating portion is in a shape of a fin arranged on a periphery portion of the housing.

5. A light irradiating unit comprising an LED and a housing into which the LED is incorporated and which has a heat dissipating portion wherein the housing has a first housing element and a second housing element each of which is joined serially along a predetermined axial line,
   and further comprising a pressing arrangement that fixes the LED with pressure between a first pressing face arranged at the first housing element side and a second pressing face arranged at the second housing element side accompanied by joining the first and the second housing elements and a positioning arrangement that positions the LED so as to align an optical axis of the LED with the predetermined axial line accompanied by joining the first and the second housing elements, wherein an elastic member is arranged between at least one of the first and the second pressing faces and the LED.

6. The light irradiating unit according to claim 5, wherein the light irradiating unit further comprises a lens mechanism that is incorporated into the housing and is so arranged that the light irradiated from the LED is focused on a light focusing portion arranged at a predetermined portion in a size of a predetermined radius through the lens mechanism.

7. The light irradiating unit according to claim 6, wherein the lens mechanism comprises a first lens that makes the light irradiated from the LED generally parallel and a second lens that focuses the light from the first lens into the light focusing portion.

8. The light irradiating unit according to claim 5, wherein the heat dissipating portion is in a shape of a fin arranged on a periphery portion of the housing.

9. A light irradiating unit comprising an LED and a housing into which the LED is incorporated and which has a heat dissipating portion wherein the housing has a first housing element and a second housing element each of which is joined serially along a predetermined axial line,
   and further comprising a pressing arrangement that fixes the LED with pressure between a first pressing face arranged at the first housing element side and a second pressing face arranged at the second housing element side accompanied by joining the first and the second housing elements and a positioning arrangement that positions the LED so as to align an optical axis of the LED with the predetermined axial line accompanied by joining the first and the second housing elements, wherein the positioning arrangement makes use of a ring portion mounted on the housing and positions the LED by inserting the LED into a center through hole of the ring portion without a slack accompanied by joining the first housing element to the second housing element.

10. The light irradiating unit according to claim 9, wherein the light irradiating unit further comprises a lens mechanism that is incorporated into the housing and is so arranged that the light irradiated from the LED is focused on a light focusing portion arranged at a predetermined portion in a size of a predetermined radius through the lens mechanism.

11. The light irradiating unit according to claim 10, wherein the lens mechanism comprises a first lens that makes the light irradiated from the LED generally parallel and a second lens that focuses the light from the first lens into the light focusing portion.

12. The light irradiating unit according to claim 9, wherein the heat dissipating portion is in a shape of a fin arranged on a periphery portion of the housing.

13. A light irradiating unit comprising an LED and a housing into which the LED is incorporated and which has a heat dissipating portion wherein the housing has a first housing element and a second housing element each of which is joined serially along a predetermined axial line, and further comprising a pressing arrangement that fixes the LED with pressure between a first pressing face arranged at the first housing element side and a second pressing face arranged at the second housing element side accompanied by joining the first and the second housing elements and a positioning arrangement that positions the LED so as to align an optical axis of the LED with the predetermined axial line accompanied by joining the first and the second housing elements, wherein the positioning arrangement makes use of a ring portion mounted on the housing and positions the LED by inserting the LED into a center through hole of the ring portion without a slack accompanied by joining the first housing element to the second housing element, and an inner face of the ring portion is a mirror finished conic concave face and the ring portion has a function to guide light forward.

14. The light irradiating unit according to claim 13, wherein the light irradiating unit further comprises a lens mechanism that is incorporated into the housing and is so arranged that the light irradiated from the LED is focused on a light focusing portion arranged at a predetermined portion in a size of a predetermined radius through the lens mechanism.

15. The light irradiating unit according to claim 14, wherein the lens mechanism comprises a first lens that makes the light irradiated from the LED generally parallel and a second lens that focuses the light from the first lens into the light focusing portion.

16. The light irradiating unit according to claim 13, wherein the heat dissipating portion is in a shape of a fin arranged on a periphery portion of a the housing.

17. A light irradiating unit comprising an LED and a housing into which the LED is incorporated and which has a heat dissipating portion wherein the housing has a first housing element and a second housing element each of which is joined serially along a predetermined axial line, and further comprising a pressing arrangement that fixes the LED with pressure between a first pressing face arranged at the first housing element side and a second pressing face arranged at the second housing element side accompanied by joining the first and the second housing elements and a positioning arrangement that positions the LED so as to align an optical axis of the LED with the predetermined axial line accompanied by joining the first and the second housing elements, wherein the LED in an elementary substance can flow electrical current not lower than 200 mA through 300 mA in a stationary state, and the second hosing element comprises a wall and a projecting a body projecting from the wall along the axial line, the LED is mounted on an annular substrate, and the second pressing face set at a distal end of the projecting body that penetrates a center hole of the substrate is tightly attached to a bottom face of the LED directly or through a heat conduction member.

18. The light irradiating unit according to claim 17, wherein the light irradiating unit further comprises a lens mechanism that is incorporated into the housing and is so arranged that the light irradiated from the LED is focused on a light focusing portion arranged at a predetermined portion in a size of a predetermined radius through the lens mechanism.

19. The light irradiating unit according to claim 18, wherein the lens mechanism comprises a first lens that makes the light irradiated from the LED generally parallel and a second lens that focuses the light from the first lens into the light focusing portion.

20. The light irradiating unit according to claim 17, where in the heat dissipating portion is in a shape of a fin arranged on periphery portion of the housing.

21. A light irradiating unit comprising an LED and a housing into which the LED is incorporated and which has a heat dissipating potion wherein the housing has a first housing element and a second housing element each of which is joined serially along a predetermined axial line, and further comprising a pressing arrangement that fixes the LED with pressure between a first pressing face arranged at the first housing element side and a second pressing face arranged at the second housing element side accompanied by joining the first and the second housing elements and a positioning arrangement that positions the LED so as to align an optical axis of the LED with the predetermined axial line accompanied by joining the first and the second housing elements, wherein the second hosing element comprises a wall and projecting a body projecting from the wall along the axial line, the LED is mounted on an annular substrate and the second pressing face set at a distal end of the projecting body that penetrates a center hole of the substrate is tightly attached to a bottom face of the LED directly or through a heat conduction member, and an elastic member is arranged between at least one of the first and the second pressing faces and the LED.

22. The light irradiating unit according to claim 21, wherein the light irradiating unit further comprises a lens mechanism that is incorporated into the housing and is so arranged that the light irradiated from the LED is focused on a light focusing portion arranged at a predetermined portion in a size of a predetermined radius through the lens mechanism.

23. The light irradiating unit according to claim 22, wherein the lens mechanism comprises a first lens that makes the light irradiated from the LED generally parallel and a second lens that focuses the light from the first lens into the light focusing portion.

24. The light irradiating unit according to claim 21, wherein the heat dissipating portion is in a shape of a fin arranged on periphery portion of the housing.

25. A light irradiating unit comprising an LED and a housing into which the LED is incorporated and which has a heat dissipating portion wherein the housing has a first housing element and a second housing element each of which is joined serially along a predetermined axial line, further comprising a pressing arrangement that fixes the LED with pressure between a first pressing face arranged at the first housing element side and a second pressing face arranged at the second housing element side accompanied by joining the first and the second housing elements, a positioning arrangement that positions the LED so as to align an optical axis of the LED with the predetermined axial line accompanied by joining the first and the second housing elements and a lens mechanism that is incorporated into the housing, wherein the LED in an elementary substance can flow electrical current not lower than 200 mA through 300 mA in a stationary state, and the positioning arrangement positions the LED by inserting the LED without a slack into a concave portion arranged on a lens constituting the lens mechanism.

26. The light irradiating unit according to claim 25, wherein the light irradiating unit further comprises a lens mechanism that is incorporated into the housing and is so arranged that the light irradiated from the LED is focused on a light focusing portion arranged at a predetermined portion in a size of a predetermined radius through the lens mechanism.

27. The light irradiating unit according to claim 26, wherein the lens mechanism comprises a first lens that makes the light irradiated from the LED generally parallel and a second lens that focuses the light from the first lens into the light focusing portion.

28. The light irradiating unit according to claim 25, wherein the heat dissipating portion is in a shape of a fin arranged on periphery portion of the housing.

29. A light irradiating unit comprising an LED and a housing into which the LED is incorporated and which has a heat dissipating portion wherein the housing has a first housing element and a second housing element each of which is joined serially along a predetermined axial line, further comprising a pressing arrangement that fixes the LED with pressure between a first pressing face arranged at the first housing element side and a second pressing face arranged at the second housing element side accompanied by joining the first and the second housing elements, a positioning arrangement that positions the LED so as to align an optical axis of the LED with the predetermined axial line accompanied by joining the first and the second housing elements and a lens mechanism that is incorporated into the housing, wherein the positioning arrangement positions the LED by inserting the LED without a slack into a concave portion arranged on a lens constituting the lens mechanism, and an elastic member is arranged between at least one of the first and the second pressing faces and the LED.

30. The light irradiating unit according to claim 29, wherein the light irradiating unit further comprises a lens mechanism that is incorporated into the housing and is arranged that the light irradiated from the LED is focused on a light focusing portion arranged at a predetermined portion in a size of a predetermined radius through the lens mechanism.

31. The light irradiating unit according to claim 30, wherein the lens mechanism comprises a first lens that makes the light irradiated from the LED generally parallel and a second lens that focuses the light from the first lens into the light focusing portion.

32. The light irradiating unit according to claim 29 wherein the heat dissipating portion is in a shape of a fin arranged on periphery portion of the housing.

* * * * *